United States Patent [19]
Boyd et al.

[11] Patent Number: 5,051,368
[45] Date of Patent: Sep. 24, 1991

[54] METHOD FOR FORMING AN AMINO ACID THIOHYDANTOIN USING AN N-SUBSTITUTED KETENIMINE ACTIVATOR

[75] Inventors: Victoria L. Boyd, San Carlos; David H. Hawke, Hayward; Timothy G. Geiser, San Mateo, all of Calif.

[73] Assignee: Applied Biosystems, Inc., Foster City, Calif.

[21] Appl. No.: 546,303

[22] Filed: Jun. 29, 1990

[51] Int. Cl.$^5$ .............................................. G01N 33/68
[52] U.S. Cl. ...................................... 436/89; 436/175; 436/178; 530/345; 530/408; 530/409; 530/810
[58] Field of Search ................. 436/89, 177, 178, 175; 530/345, 408, 409, 810

[56] References Cited

U.S. PATENT DOCUMENTS 4,935,494  6/1990  Miller ................................ 436/89 X

FOREIGN PATENT DOCUMENTS

0217634A2  4/1987  European Pat. Off. .

OTHER PUBLICATIONS

Tarr, G. E., Methods in Protein Sequence Analysis (1988), Section 4.1: "The Long Search for a Viable Method of C-Terminal Sequencing", pp. 129–151, B. Wittman-Leibold, Ed. Proceedings of the 7th International Conf., Berlin.

Hawke, D. H., et al., Microsequence Analysis of Peptides and Proteins: Trimethylsilylisothiocyanate as a Reagent for COOH-Terminal Sequence Analysis (1987) Analytical Biochem. 166, pp. 298–307.

Yamashita, S., Sequential Degradation of Polypeptides from the Carboxy-End Peptide Bonds (1971), Biochem. Biophys. Acta, 229 pp. 301–309.

Bailey, J. M., et al., Carboxy-terminal Sequencing: Formation and Hydrolysis of C-terminal Peptidylthiohydantoins (1990), Biochemistry vol. 29, No. 12, pp. 3145–3156.

Miller, C. G., et al., "Studies on the Use of Silyl Compounds for Protein Carboxy-Terminal Sequence Analysis", (1989), Techniques in Protein Chemistry, pp. 67–78, T. E. Hugh, Ed., Academic Press.

Kenner, G. W., et al., in Peptides IV, 136 "Selective Removal of the C-terminal Residue as a Thiohydantoin", (1953) J. Chem. Soc.

Primary Examiner—Robert J. Hill, Jr.
Attorney, Agent, or Firm—Peter J. Dehlinger

[57] ABSTRACT

A method of forming an amino acid thiohydantoin from an N-protected amino acid or the C-terminal amino acid of an N-protected peptide. The amino acid is activated by reaction with a ketenimine, and the activated ester is converted to the thiohydantoin by reaction with silyl or pyridine isothiocyanate. The ketenimine is generated by treating an N-substituted isoxazolium compound, such as Woodwards Reagent K with a base, preferably in the presence of the amino acid. Also disclosed is a solid phase support having a derivatized N-substituted isoxazolium or ketenimine group for use in the method.

16 Claims, 11 Drawing Sheets

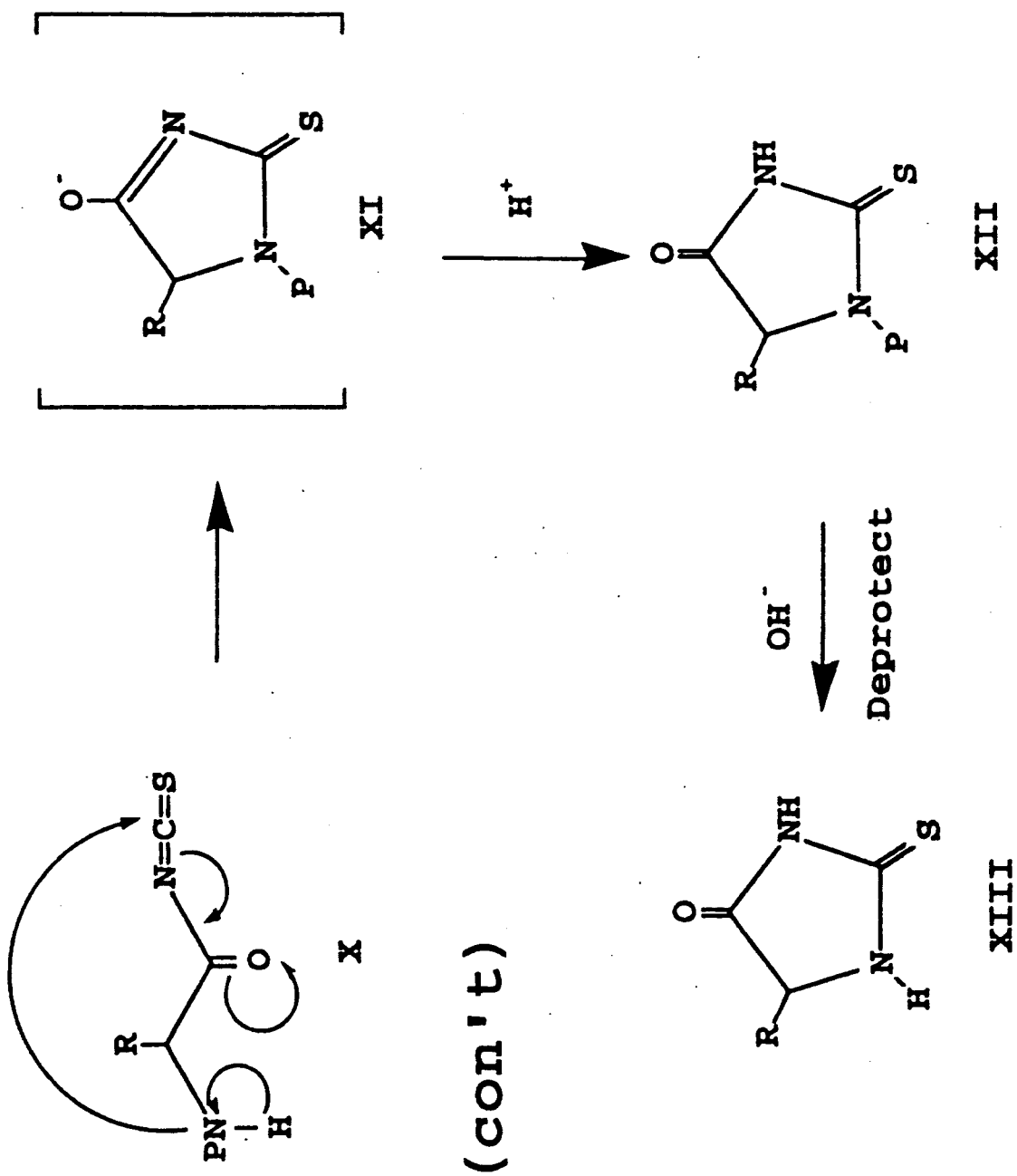
Fig. 3 (con't)

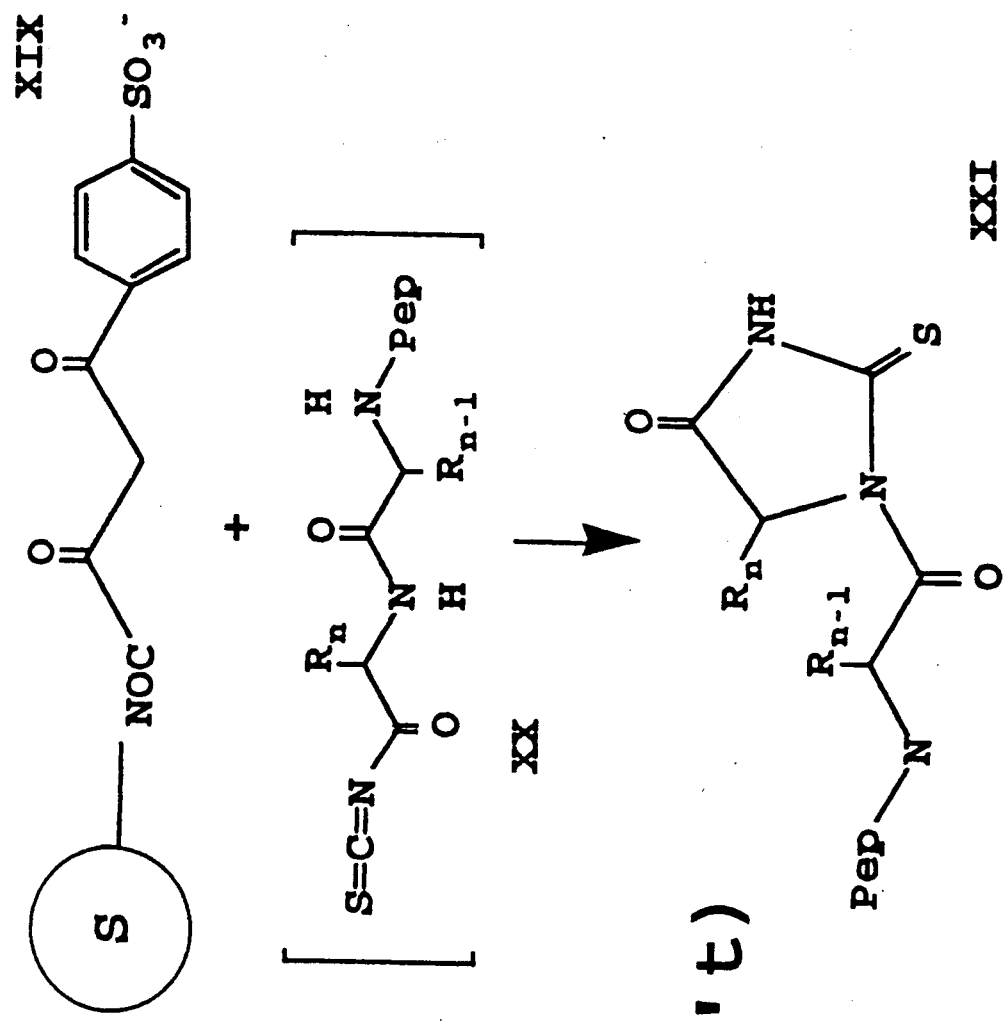
Fig. 6 (con't)

METHOD FOR FORMING AN AMINO ACID THIOHYDANTOIN USING AN N-SUBSTITUTED KETENIMINE ACTIVATOR

1. FIELD OF THE INVENTION

The present invention relates to a method and a solid-phase support for forming an amino acid thiohydantoin via ketenimine activation of the amino acid carboxyl group.

2. REFERENCES

Green, T., Protecting Groups in Organic Synthesis, Academic Press.

Hawke, D. H., et al., *Anal Biochem*, 166, p. 298 (1987).

March, J., Advanced Organic Chemistry 3$^{rd}$ ed., p. 294, Wiley, 1985.

Meuth, J. L., Biochemistry, 16:3750 (1982).

Miller, C. D., et al., in Techniques in Protein Chemistry (Hugh, T. E., ed), Academic Press, pp. 67–78 (1989).

Miller, C. G., et al., *Abstract T188 from the Third Symposium of the Protein Society*, Seattle, Wash. (July 29–Aug. 2, 1989).

Rangarajan, M., in Protein/Peptide Sequence Analysis: Current Methodologies (Bhown, A. S., ed.), CRC Press, pp. 136–144 (1988).

Shively, J. E., et al, *TIBS* 14, p. 246 (1989).

Stark, G. R., in *Methods in Enzymology* (Hirs, C. H. W., et al., eds.), Vol. 25, p. 369, Academic Press (1972).

Tarr, G. E., in Methods in Protein Sequence Analysis, (Whittmann-Liebold, B., ed) Springer Verlag, pp. 129–151 (1988).

Woodman, et al., J Org Chem, 38:4288 (1973).

Woodward, R. B., et al., Tetrahedron, Supp No. 7, pp. 415–440.

3. BACKGROUND OF THE INVENTION

A variety of methods for forming an amino acid thiohydantoin (TH), either for use in C-terminal peptide sequencing, or for use in generating standards for C-terminal sequencing procedures, have been proposed. In one general method, the amino acid (or peptide) is activated at its carboxyl terminus with an anhydride, such as acetic anhydride, in the presence of a thiocyanate (ITC) salt or acid, to form a C-terminal peptidyl-TH via a C-terminal ITC intermediate (Stark, 1972). The peptidyl-TH can be cleaved to produce a shortened peptide and a C-terminal amino acid TH, which can be identified, e.g., by high pressure liquid chromatography (HPLC). The coupling conditions in this method typically require about 90 minutes at a 60°–70° C. (Meuth), and often lead to degradation of amino acid side chains in the peptide. For example, the side chain hydroxyl groups of serine and threonine may be attacked by the anhydride, requiring hydroxyl group protection.

A thiohydantoin formation method which can be carried out under milder conditions has been described by the inventor and co-workers (Hawke). Using trimethylsilyl isothiocyanate (TMS-ITC) as the reagent, TH formation was achieved by activation of the peptide with acetic anhydride for 15 min at 50° C., followed by reaction with TMS-ITC for an additional 30 min at 50° C. Despite the milder reaction conditions, the method nonetheless involves peptide exposure to a highly reactive anhydride activating agent, resulting in undesired side chain modifications.

4. SUMMARY OF THE INVENTION

It is one object of the present invention to provide a method for producing an amino acid thiohydantoin under relatively mild reaction conditions.

In the method of the invention, an N-protected amino acid is activated by reaction with a ketenimine to form the corresponding activated ester of the amino acid, and the activated ester is reacted with a silylisothiocyanate or pyridinium thiocyanate to form the desired amino acid thiohydantoin. The ketenimine is preferably formed by treating an N-substituted isoxazolium, such as Woodward's Reagent K (WRK) or a related 2-alkyl-5'-alkyl or aryl isoxazolium compound with a base in the presence of the amino acid. The silylisothiocyanate is preferably a trialkylsilylyisothiocyanate, such as trimethylsilylisothiocyanate (TMSITC).

In one embodiment, the ketenimine is derivatized on a solid support, allowing amino acid or peptidyl TH formation in an immobilized-reagent system. The support is preferably formed by base treating a solid-phase support derivatized with an N-substituted isoxazolium, immediately prior to use.

The method is applicable for C-terminal peptide sequencing. Here the N-protected amino acid which is reacted with the ketenimine is the C-terminal residue of the peptide, forming an activated ester at the N-terminal carboxyl group of the peptide. The activated ester is contacted with an isothiocyanate to form a corresponding C-terminal peptidyl thiohydantoin (TH). The peptidyl TH is cleaved to release the C-terminal amino acid TH from the residual peptide, and the amino acid TH is isolated and identified.

In another aspect, the invention includes a solid-phase support derivatized with N-substituted isoxazolium compound or ketenimine compound, for use in the invention.

These and other objects and features of the invention will become more fully apparent when the following detailed description of the invention is read in conjunction with the accompanying drawings.

DETAILED DESCRIPTION OF THE INVENTION

A. Amino Acid Thiohydantoin Formation in Solution Phase

The section describes solution-phase reactions involved in (i) generating a reactive N-substituted ketenimine, (ii) activating an N-protected amino acid or peptide with the ketenimine, and (iii) reacting the activated amino acid or peptide with a silyl or isothiocyanate (ITC) or pyridinium thiocyanate to form the desired amino acid or peptidyl thiohydantoin (TH).

Figure 1:
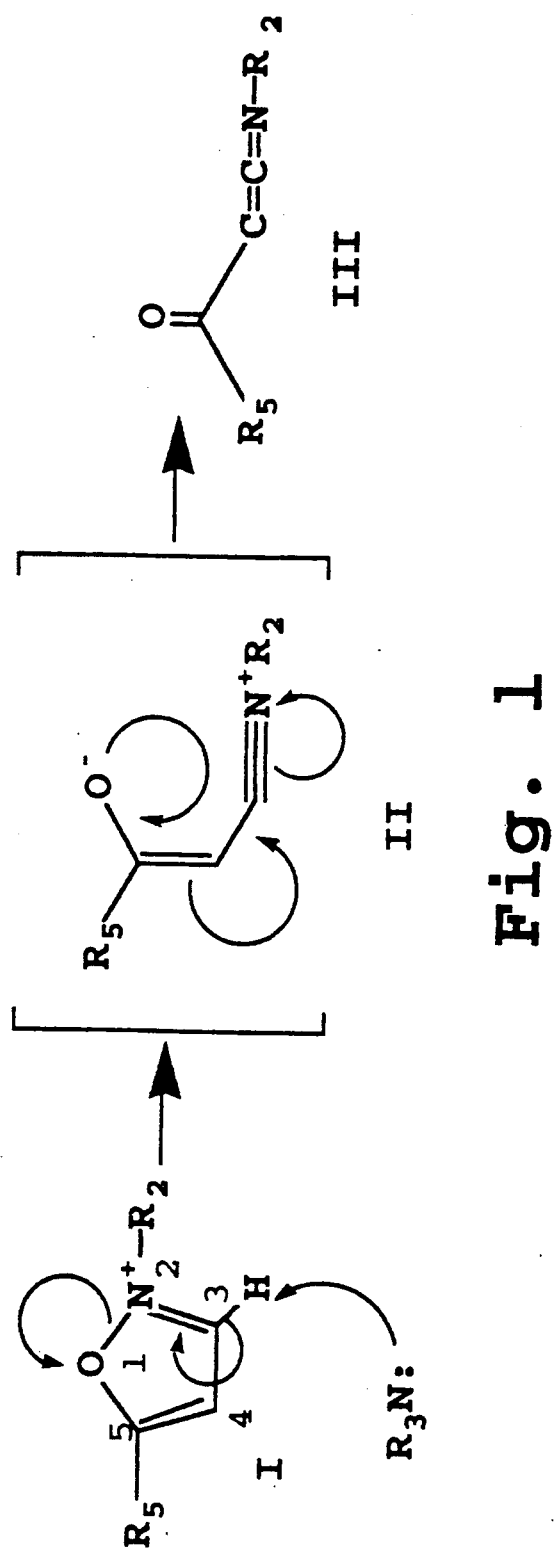
FIG. 1 shows the conversion of an N-substituted isoxazolium compound (I) to the corresponding ketenimine (III) in the presence of base, via an intermediate (II)

FIG. 1 illustrates one preferred method for generating a reactive N-substituted ketenimine for use in the invention. The reaction involves the conversion of an N-substituted isoxazolium compound to the corresponding ketenimine compound by ring opening in the presence of a base, e.g. ($R_3N$), as has been described (Woodward). The reaction likely proceeds through the intermediate (II) shown in the figure.

The $R_2$, (N-substitution) group may be a methyl, ethyl, t-butyl or similar alkyl group or a phenyl, substituted phenyl or related aryl group. The compound must be N-substituted, i.e., $R_2$ is not hydrogen, to give the desired ketenimine. Position 3 of the isoxazolium compound must be hydrogen, to allow conversion to the ketenimine. Position 5 may be phenyl, substituted phenyl, such as sulfophenyl (Woodwards Reagent K), or alkyl, such as methyl (Woodwards Reagent L). That is, the 5'-substitution may be either alkyl or aryl. Position 4 may be substituted with an alkyl group, such as methyl. However, anomalous results may be obtained if both the 4 and 5 positions are substituted, e.g., where $R_5$ is phenyl, and $R_4$ is methyl (Woodman).

One preferred class of N-substituted isoxazolium compounds includes 2-alkyl-5'-alkylisoxazolium salts, such as 2-t-butyl, 5'-methylisoxazolium (Woodwards Reagent L or WRL), or 2-alkyl-5'-arylisoxazolium salts, such as 2-ethyl-5'-phenylisoxazoliumsulfonate (Woodwards Reagent K or WRK). Several of these compounds are commercially available or may be prepared by published methods (Woodward). The sulfonate group in WRK makes the compound zwitterionic, and confers increased solubility. Because of its instability, the ketenimine is preferably generated in the presence of the N-protected amino acid or peptide, as described below.

Figure 2:
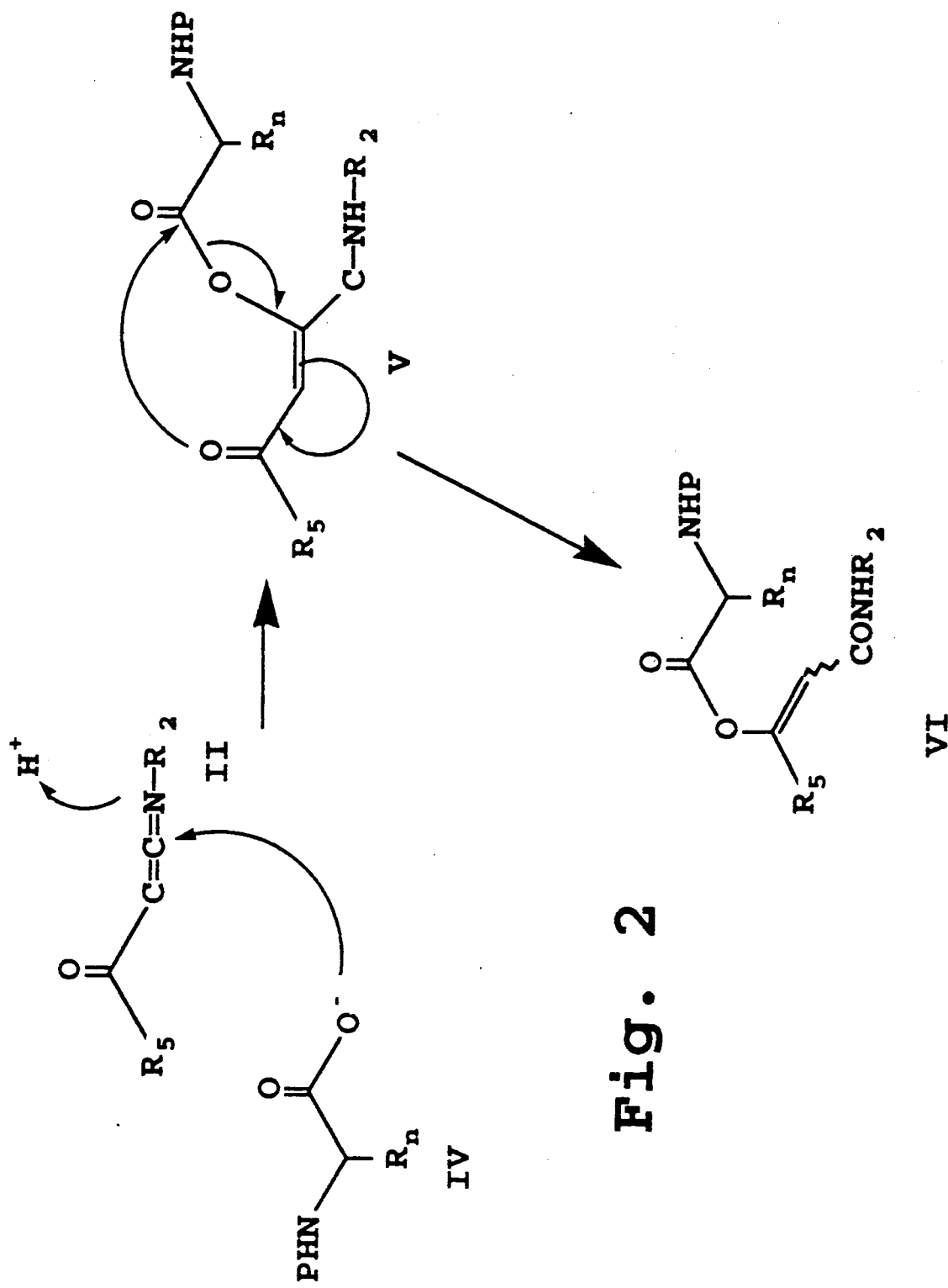
FIG. 2 illustrates the reaction of an N-protected amino acid (IV) with the FIG. 1 ketenimine (III) to form an activated amino acid ester (VI), through a possible reaction intermediate (V)

The reaction of the ketenimine with an N-protected amino acid is shown in FIG. 2. The protecting group P on the amino acid (or on the peptide) is one, such as FMOC (fluorenylmethoxycarbonyl), t-BOC (t-butyloxycarbonyl), t-Bu (t-butyl), or Mtr. Such protecting groups are commercially available (e.g., Aldrich Chemical Co.), or may be readily synthesized by published methods (Green). Ser, Thr, Asp, Glu may be protected by t-Bu; Lys by t-BOC; and Arg, by Mtr. Selected protecting groups may be removed, if desired, after enol ester formation, but before reaction with the ITC compound. The N-protecting group is removed after thiohydantoin formation.

The activation reaction is typically performed in an anhydrous non-nucleophilic solvent, such as anhydrous acetonitrile (MeCN) containing the N-protected amino acid and enough base to ensure the amino acid carboxyl group is deprotonated. To that solution is added one equivalent each of the isoxazolium salt and a tertiary amine, e.g., diisopropylethylamine (DIPEA). The solution is then stirred for several hours at room temperature, until a homogeneous solution is observed, to form the amino acid-WRK-activated ester (VI), as illustrated in FIG. 2. After the activated ester has formed, the solution may be concentrated and dried.

Figure 3:
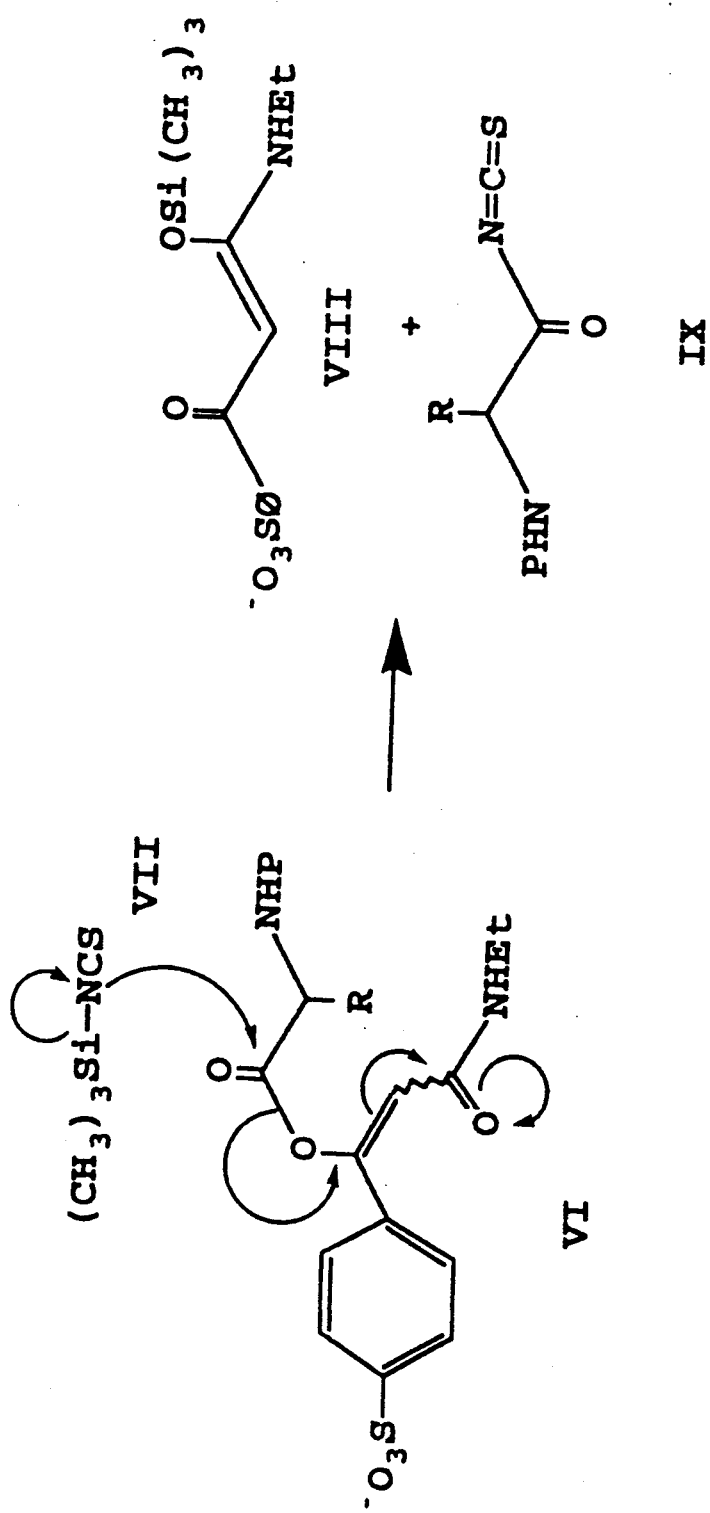
FIG. 3 shows the reaction of trimethylsilylisothiocyanate (TMSITC) (VII) with the activated amino acid ester (VI) to form the corresponding amino acyl ITC (X), and the rearrangement of the ITC to form the amino acid TH (XII).

The activated ester is resuspended in anhydrous non-nucleophilic solvent, e.g., methylene chloride ($CH_2Cl_2$), and a slight molar excess of a selected isothiocyanate (or thiocyanate) is added, leading to the cyclization and thiohydantoin formation illustrated in FIG. 3. The reaction mixture is stirred at room temperature. The progress of the reaction may be followed by any of several well-known means, such as thin-layer chromatography, or HPLC.

The product thiohydantoin may be purified by one of several known methods, such as silica-gel chromatography HPLC. The N-protecting group may be removed by standard methods (Green). For example, FMOC-Ile thiohydantoin may be purified by column chromatography on silica gel eluting with a methylene chloride:methanol solvent mixture (9:1 $CH_2Cl_2$:MeOH). The FMOC group may be removed by reaction with 20% piperidine in acetonitrile to provide, after column chromatography and recrystallization, moderate yields.

Reactive thiocyanates or isothiocyanate compounds which have been found to be effective in the present method are silylisothiocyanates and pyridinium thiocyanate. Preferred silylisothiocyanates are trialkylsilylisothiocyanates, such as trimethylsilylisothiocyanate (TMSITC). The silyl ITC are more reactive nucleophiles than metal ITC salts, presumably due to the polarizability of the Si-N bond. The reactivity of the pyridinium thiocyanate compound may be due in part to the ability of pyridine to act as a nucleophilic acrylation catalyst (March).

Metal thiocyanates (i.e., potassium-, sodium-, or lead-isothiocyanate) and ammonium thiocyanate (TC) were tested for reactivity in the present method, but were not very effective in thiohydantoin formation.

It has also been found that the solvent's polarity plays a role in the TH formation reaction (i.e., the series of steps shown in FIG. 2). Generally, cyclization reactions performed in solvents having greater polarity than $CH_2Cl_2$ work less well. For example, TH formation reactions done in N-methylpyrrolidone (NMP) or dimethylformamide (DMF) did not produce measurable amounts of TH product.

FIGS. 2 and 3 illustrate possible reaction mechanisms for formation of activated amino acid ester by reaction with a reactive ketenimine (FIG. 2) and reaction of the activated ester with a silyl ITC to form the desired amino acid TH. With reference to FIG. 2, the central carbon of the kentenimine (III) is attacked by the N-protected amino acid carboxylate (IV) and rearranges, through a presumed intermediate (V), to form the amino acid enol ester VI.

The proposed sequence of TH formation is shown in FIG. 3. The enol ester VI is attacked by the ITC (VII) to form compound VIII and amino acyl isothiocyanate (IX). The nitrogen of the amino acid attacks the thiocarbonate carbon (X) to form a presumed intermediate N-protected amino acyl thiohydantoin (XI) which equilibrates to the more stable TH isomer XII. Removal of the protecting group using known procedures (Example 1) yields the desired amino acid TH (XIII). Here it is noted that the reaction conditions employed may not require amino acid side-chain protection, thus allowing amino acid TH formation without the additional step of side-chain deprotection.

In another aspect, the solution-phase method just described may be used in forming a C-terminal amino acid thiohydantoin of an N-protected peptide. In this reaction, the residual peptide (N-protected peptide less its C-terminal residue) substitutes for the N-protecting group P in the above reactions.

B. Amino Acid Thiohydantoin Formation on Solid Phase

The section describes solid-phase reactions involved in (i) generating a reactive ketenimine on a solid support, (ii) activating an N-protected amino acid or peptide, by reaction with the activated support, and (iii) reacting the activated amino acid or peptide on the support with a silyl ITC or pyridine thiocyanate to form the desired amino acid or peptidyl (TH).

Figure 4:
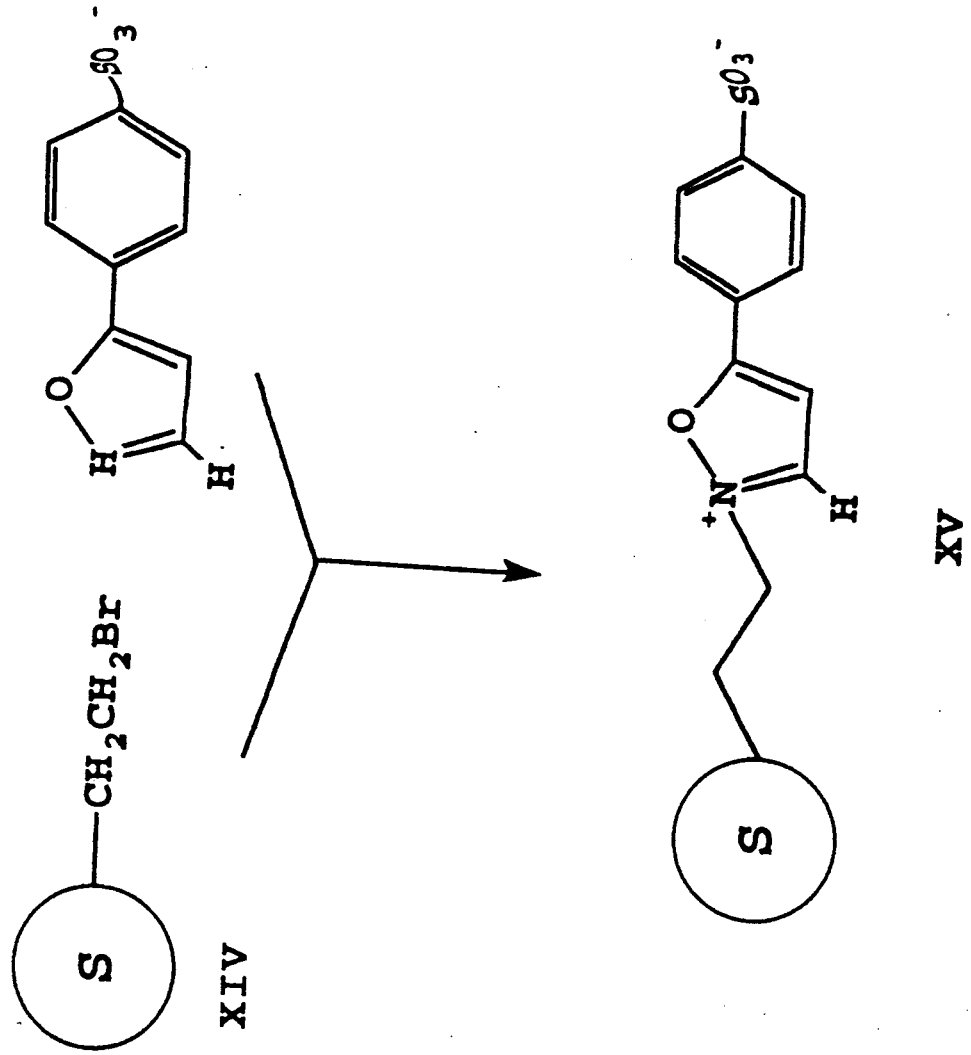
FIG. 4 illustrates steps for derivatizing a solid support having alkylating groups (XIV) with an isoxazole.

FIG. 4 illustrates a coupling reaction for forming a solid support derivatized with an N-substituted phenylisoxazolium salt. The support may be particle beads, or a membrane support, or the like, derivatized with suitable chemical groups. Bead or membrane support materials, such as glass or polymer material such as nylon, polystyrene, polyethylene, Teflon TM, having reactive chemical groups, such as amine, carboxyl, and hydroxyl groups, are commercially available.

The solid support (XIV) in FIG. 4 is a particle bead or the like, indicated at S, having surface alkylating groups.

The bead is derivatized with the N-substituted isoxazolium compound by reacting the support with an isoxazole, such as the compound shown at the right in FIG. 4. The reaction is carried out in a suitable solvent, such as acetonitrile. Silver ion ($Ag^+$) may be included to aid the reaction. Conventional alkylation reaction conditions are employed. The derivatized support is shown at (XV) in FIG. 4.

Figure 5:
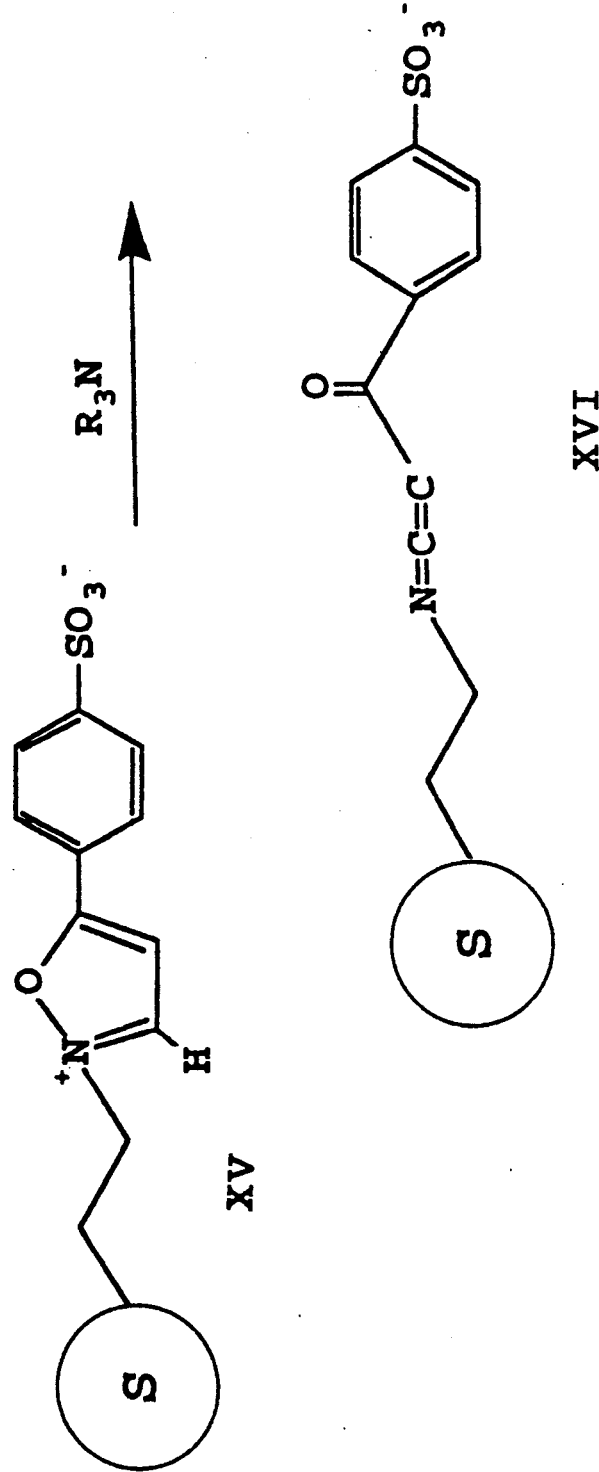
FIG. 5 shows the conversion of an immobilized phenyl isoxazolium compound derivatized on a solid support (XV) to form the corresponding support bearing ketenimine groups (XVI)

The support is activated by treatment with a base to generate reactive ketenimine groups on the support, as illustrated in FIG. 5. The activation reaction is preferably carried out in the presence of N-protected amino acid, as detailed above, forming the amino acid enol ester shown at the bottom in FIG. 2, but where the activated amino acid is now coupled to a solid support.

The support and bound amino acid enol ester may be washed, e.g., with methylene chloride, to remove unbound reactants, and the particles dried. The dried support is now suspended in a solution of a suitable reagent, such as TMSITC, and the suspension is allowed to react to form the corresponding amino acid TH in solution. With reference to FIG. 3, it will be appreciated that the ITC reaction releases the activated amino acid from the support, with subsequent cyclization in the solution phase leading to the amino acid TH. The byproducts of the ketenimine moiety are retained on the support, and the amino acid TH and the products of the ITC reagent are in the solution phase. The amino acid TH can be purified from the other solution phase components by standard methods, as noted in Section A.

Figure 6:
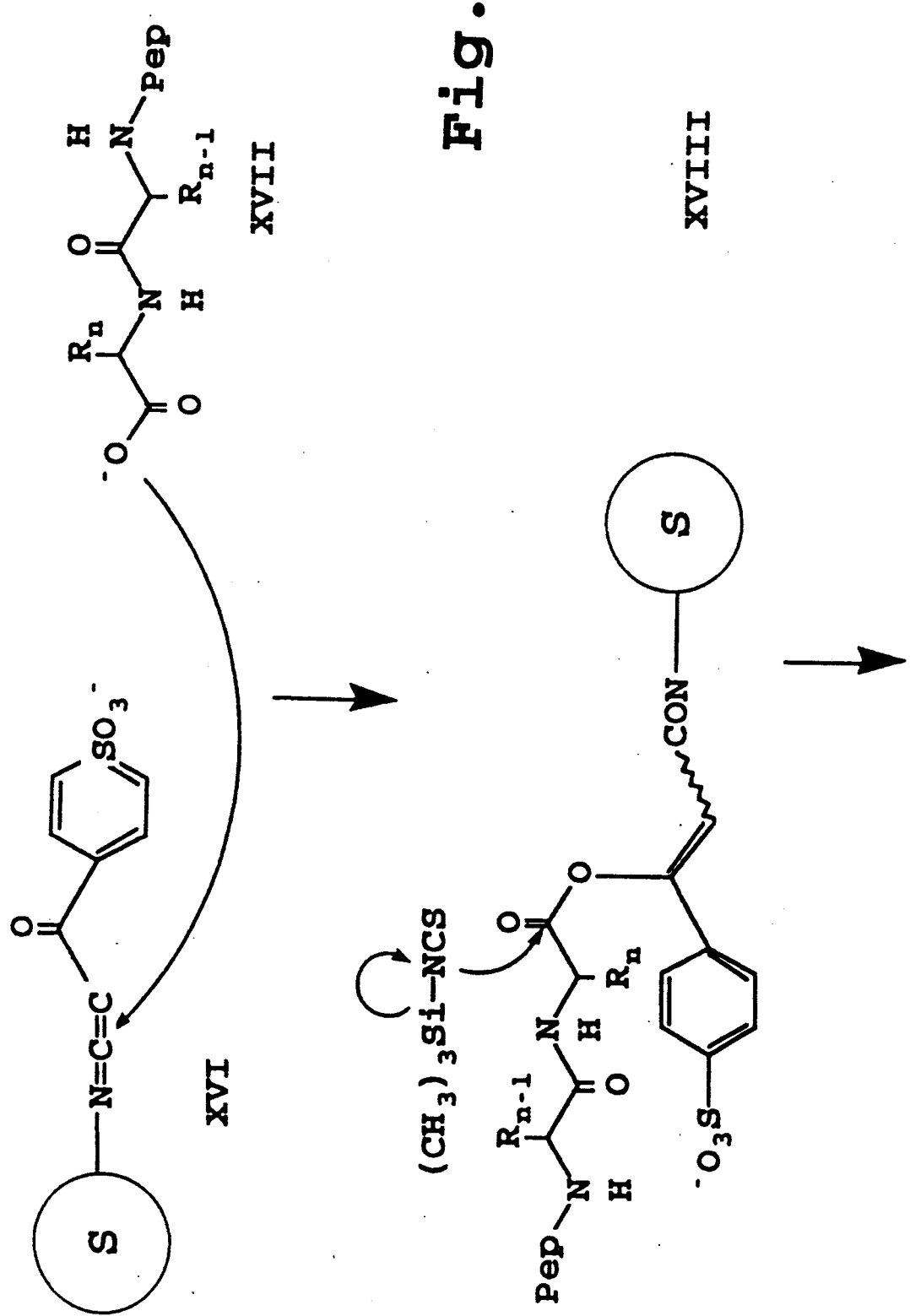
FIG. 6 illustrates the reaction of a peptide with the FIG. 5 activated support (XVI) and TMSITC to form a peptidyl TH (XXI)

The solution-phase method (immobilized reagent) may be used in forming a C-terminal amino acid TH of a N-protected peptide, substituting the N-protected peptide for an N-protected amino acid in the above-described reaction methods. FIG. 6 illustrates the steps in the formation of a peptidyl TH from an N-protected peptide having a C-terminal amino acid with an $R_n$ side group, and an amino acid residue penultimate to the C-terminus with an $R_{n-1}$ side chain.

The reaction shown at the top in the figure is carried out by reacting the N-protected peptide (XVII) with the activated support, preferably under reaction conditions like those described above in which the ketenimine is generated and reacted with the peptide in a single step. After washing the support, the peptidyl enol ester (XVIII) attached to the support is reacted with a silyl ITC, releasing the peptidyl ITC compound in solution form (XX), with subsequent cyclization yielding the desired peptidyl TH (XXI). The application of this reaction to C-terminal sequencing is described in Section C below.

Also forming part of the invention are the derivatized supports used in the method. These include a solid-phase support derivatized with an N-substituted phenylisoxozolium salts, and same support after base activation, now derivatized with reactive ketenimine groups.

C. Cleavage and Identification of C-Terminal TH

In one aspect, the method of the invention is used for C-terminal peptide sequencing, by (a) forming a peptidyl TH in accordance with the above method, and (b) releasing, isolating, and identifying the C-terminal amino acid TH.

A variety of cleavage reactions for releasing a C-terminal TH from a peptidyl TH are known. Hydrolytic cleavage with 12 N HCl, dilute alkali (Kenner), or saturated aqueous triethylamine have been reported. These cleavage reactions are reported to yield up to 70% cleavage, but the extreme pH conditions can lead to thiohydantoin ring opening and/or damage to peptide side chains. More recently, cleavage by treatment with acetohydroxamate in pyridine at pH 8.0 was reported (Meuth). This method affords recovery yields of up to 60-80% of the C-terminal thiohydantoin (Miller, 1988). A related method involves treatment with primary or secondary amines in acetonitrile.

The cleavage reactions are typically carried out at room temperature or greater for a few minutes to one hour, depending on the cleavage reagent used. The course of the reaction can be readily followed, for example, by HPLC, for the purpose of optimizing thiohydantoin release and minimizing unwanted side reactions (e.g., ring opening).

In one preferred solution-phase cleavage method, the peptidyl TH is treated with 10% propylamine in acetonitrile at room temperature for 15 minutes. In a related method, the peptidyl TH was cleaved with tetra-N-butylamonium hydroxide in water containing 1 mg/ml dithiothreitol (DTT).

Figure 7:
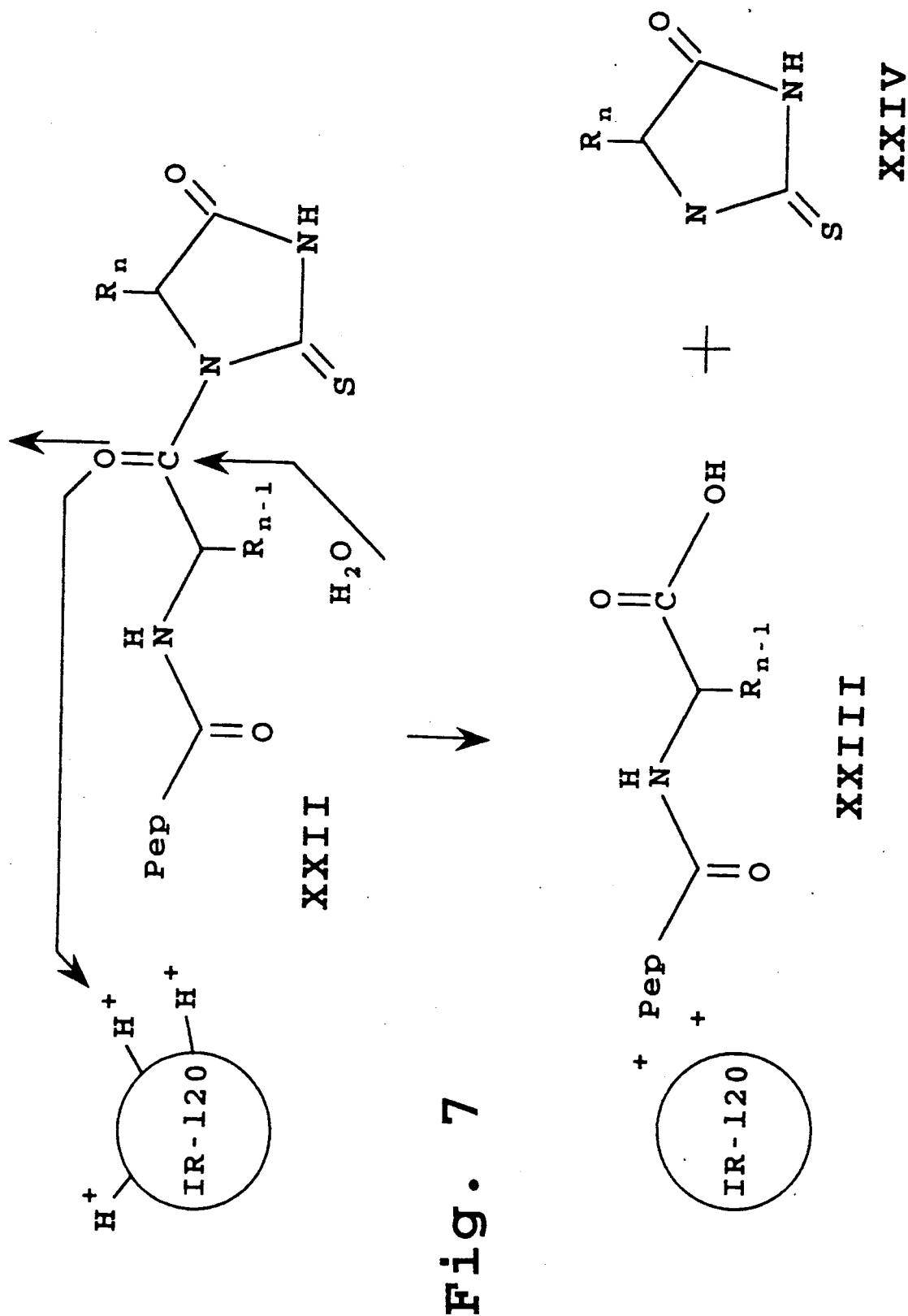
FIG. 7 illustrates the steps in cleaving a peptidyl TH by a cation-exchange resin, and retention of the residual peptide to the resin support.

Alternatively, the cleavage reaction may be carried out by contacting the peptidyl TH in a suitable solvent with an immobilized cleaving reagent. One immobilized cleavage reagent which has been reported (Yamashita) is a cation-exchange resin Amberlite® IR-120 (XI) (protonated form), available from Aldrich (Milwaukee, WI). As illustrated in FIG. 7, the resin promotes the acid-catalyzed hydrolysis of the peptidyl TH (XXII), yielding the desired amino acid TH (XXIV) and residual peptide (XXIII). Typically, the peptidyl TH sample is added to the resin (about 2 meq $H^+$ available per gram resin), and the mixture is incubated for 2-6 hours at room temperature. The peptide solution is prepared typically by removing the solvent used in peptidyl TH formation by vacuum, and redissolving the peptidyl TH in the aqueous medium.

The residual peptide may be bound to the cation-exchange resin, allowing the free amino acid TH to be separated from the residual peptide, by washing the resin under low ionic strength conditions. With the residual peptide bound to the support, the free amino acid TH can be obtained by washing or elution in substantially purified form. The residual peptide may be released subsequently by eluting at elevated ionic strength or pH.

The residual peptide and amino acid TH formed as above may alternatively be separated, if necessary, by passage through a anion exchange resin, or by chromatography, for example, by HPLC or molecular sieve chromatography.

In a second general embodiment, the cleavage reagent is derivatized with a chemical group capable of reacting with the peptidyl TH, to release free amino acid TH and link the residual peptide covalently. The free amino acid TH can then be isolated in substantially purified form by washing or elution, and the residual peptide can be released by hydrolytic cleavage of the peptide from the support.

Figure 8:
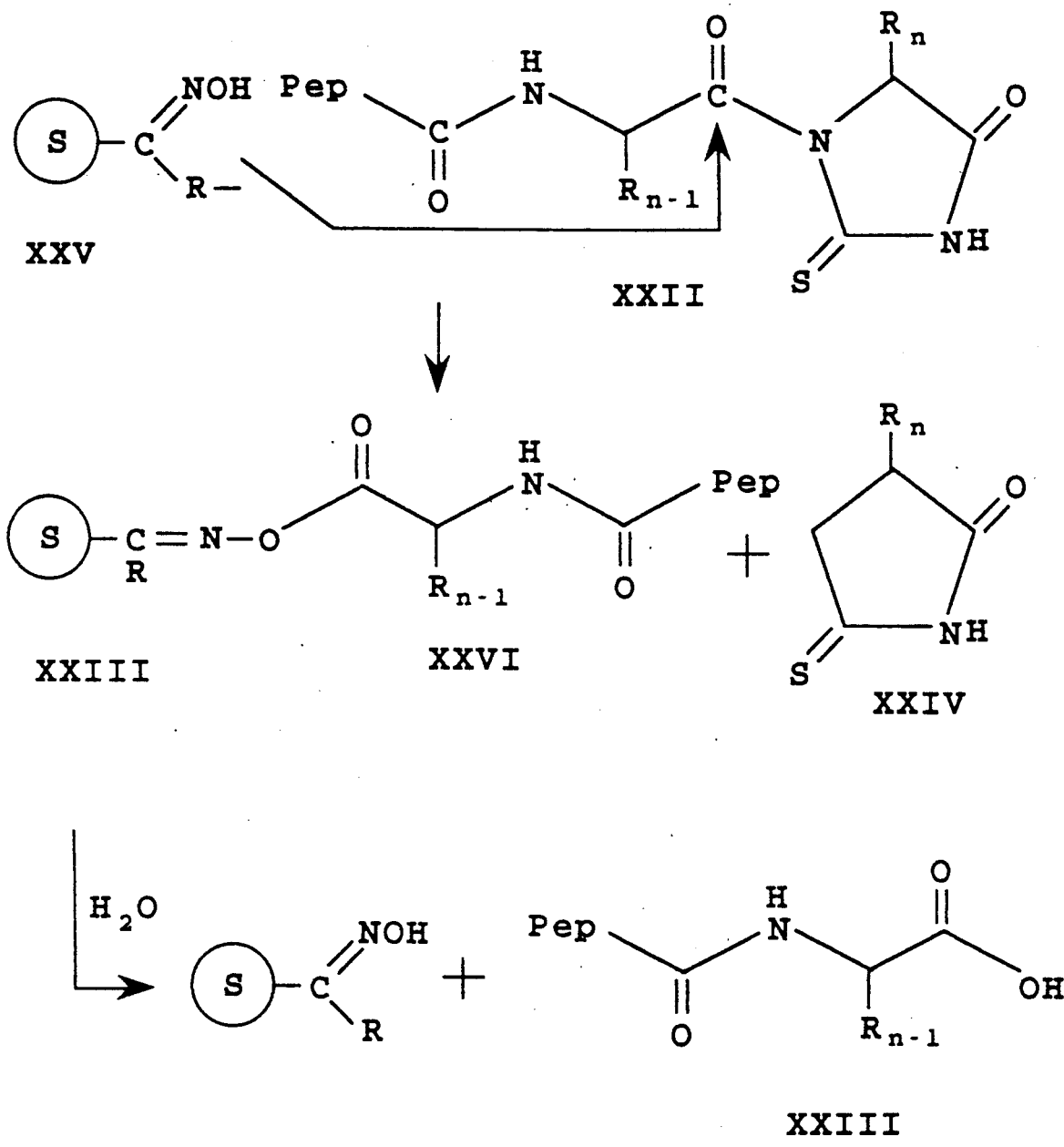
FIG. 8 illustrates the steps in cleaving a peptidyl TH by a solid support derivatized with oxime groups, and subsequent hydrolytic release of the residual peptide from the resin support.

One exemplary solid-phase cleavage reagent is the oxime-derivatized solid support (XXV) shown in FIG. 8. Such a support reagent may be obtained from Chemical Dynamics (Plainfield, N.J.). The R group in the figure may be an alkyl or aryl group, or H. One commercially available support has a nitrophenyl R group. As shown, hydrolytic cleavage of the peptidyl TH by the oxime group on the support couples the residual peptide to support (XXVI), with the release of free amino acid TH (XXIV). The reaction is preferably carried out in an aprotic solvent, such as acetonitrile, for 15 to 120 minutes at room temperature.

After recovery of the amino acid TH, and washing the solid support, the residual peptide can be hydrolytically released from the support by contact with acidified aqueous acid or base, as indicated at the bottom in FIG. 8. Thus the method allows for isolation of amino acid TH and residual peptide separately, the latter in substantially purified form free of reactants and side products.

The released amino acid TH compound may be identified by known chromatographic methods, such as high pressure liquid chromatography (HPLC), according to standard procedures. Compound identification can be made conveniently by comparing the run times in the columns with the run times of known reference amino acid TH's, prepared according to standard methods, or by the method of preparing an amino acid TH described above. Alternatively, the released and isolated amino acid TH can be identified by other available methods, such as mass spectrometry or NMR.

D. C-Terminal Solution-Phase Sequencing

This section describes the application of the above method to a C-terminal solution-phase sequencing method which is suitable for automated or semi-automated operation. As used herein, "solution phase sequencing" refers to sequencing reactions in which the peptide is retained in solution, and recycled successively through solid-phase (immobilized) reagents. This is in contrast to solid-phase sequencing, where the peptide is immobilized on a solid support, and is repeatedly exposed to solution-phase C-terminal residue activating and cleavage reagents.

Figure 9:
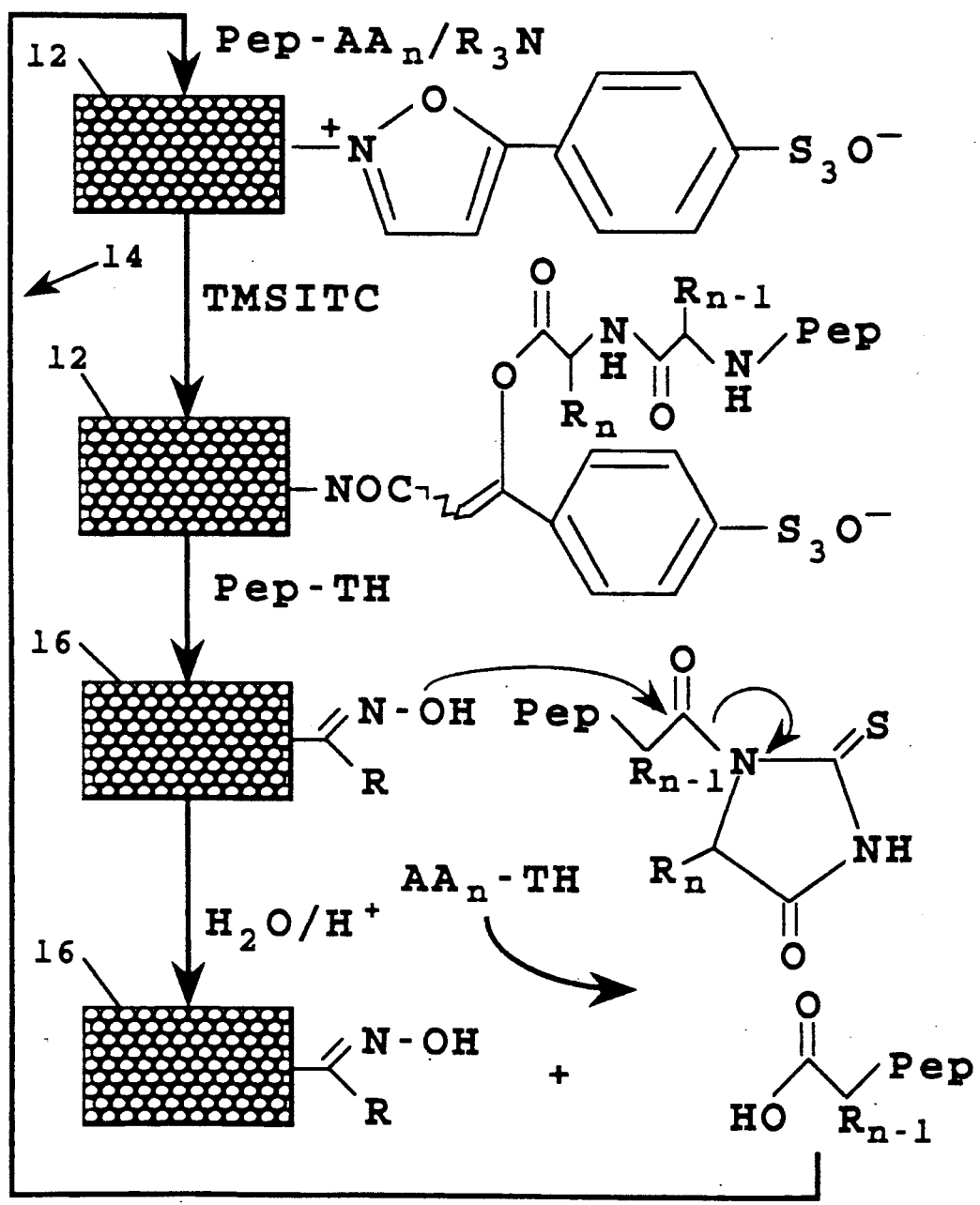
FIG. 9 illustrates the steps in a C-terminal sequencing operation in accordance with the invention.

FIG. 9 illustrates the general sequencing scheme as it is applied to a peptide Pep-$AA_n$, i.e., a peptide having n residues and a C-terminal residue $AA_n$. Initially, the peptide is dissolved in a suitable solvent, such as acetonitrile, and added with a base to the isoxazolium-derivatized solid-support resin contained in a packed column indicated at 12. Column 12 is preferably part of a two-stage cartridge 14 which also includes a column 16 containing a solid-support cleavage reagent.

After reacting the peptide with the activated support, the reaction solution, which contains the base and unbound reactants is removed by washing, and an ITC compound is added to the column, to release the attached peptide and form the peptidyl TH in solution phase.

The solution phase is then added to the second column, for the C-terminal residue cleavage step. Optionally, the two columns may be separated by an intermediate chamber (not shown), where the column 12 solvent may be removed by vacuum and replaced by a second solvent before sample introduction into column 16. In a preferred embodiment, the solid-support reagent is the type illustrated in FIG. 8. This support has the advantages that (a) the cleavage reaction can be carried out in the same non-aqueous solvent or solvent mixture used in the column-12 reaction, and (b) the binding to and release from the support of the residual peptide to the support is covalent, and therefore not dependent on the charge characteristics of the peptide.

The cleavage reaction is carried out under conditions as described above, after which the C-terminal amino acid TH ($AA_n$-TH) is eluted from the column and identified, e.g., by HPLC. Subsequently, the column is washed with an aqueous medium to release the bound residual peptide (Pep-$AA_{n-1}$).

The residual peptide obtained from the first sequencing cycle is dried, redissolved in a suitable reaction buffer, and introduced into a new cartridge. The second sequencing cycle yields an amino acid TH of the penultimate C-terminal residue ($AA_{n-1}$-TH) and a residual peptide shortened by two C-terminal residues. The sequencing cycle is repeated until the desired number of C-terminal residues have been identified.

The total number of C-terminal residues which can be identified with high confidence will vary according to the degree to which the peptide is converted to the desired peptidyl-TH in the first reaction column, and the degree to which the peptidyl-TH is cleaved in the second reaction column.

From the foregoing, it can be appreciated how various objects and features of the invention are achieved. The reaction conditions for TH formation are relatively mild, in contrast to prior art methods involving anhydride activation, and also specific for carboxyl groups, reducing the extent of unwanted side chain reactions.

The method may be readily adapted for solution-phase chemistry, thus simplifying the reaction and product isolation steps, and also allowing for solution-phase sequencing in which the amino acid TH and residual peptide are obtained in substantially pure form.

The following examples are intended to illustrate the synthesis of various acyl compounds, and their use in determining C-terminal amino acid groups, and for C-terminal sequencing. The examples are in no way intended to limit the scope of the invention.

EXAMPLE 1

Preparing Isoleucine TH: Solution-Phase Method

One millimole of FMOC-isoleucine (Applied Biosystems, Foster City, Calif.) was dissolved in acetonitrile with WRK (1 mmole) (both purchased from Applied Biosystems, Foster City, Calif.) and DIPEA (2 mmole). The reaction mixture was allowed to stir at room temperature for 2-4 hours, until a homogenous solution formed. The solution was concentrated under vacuum, and the product FMOC-Ile-WRK ester was dissolved in methylene chloride ($CH_2Cl_2$), dried over $MgSO_4$, and filtered. Next, a slight excess of trimethylsilylisothiocyanate (TMS-ITC) was added and the reaction mixture stirred overnight at room temperature. Diastereomerically pure FMOC-Ile thiohydantoin was isolated by column chromatography (9:1 $CH_2Cl_2$:MeOH).

The FMOC protecting group was removed by stirring the purified thiohydantoin in a solution containing acetonitrile and 20% piperidine for 15 minutes at room temperature. Column chromatography of the product (same system) gave the purified Ile TH.

EXAMPLE 2

Cleavage of C-terminal Peptidyl Thiohydantoins

The C-terminal thiohydantoin of FMOC-MetThr is prepared as described in Example 1 above, substituting the N-protected dipeptide Met-Thr for the N-protected Leu in Example 1. The C-terminal thiohydantoin is cleaved from the peptide by reaction in 10% propylamine/acetonitrile at room temperature for 15 minutes. HPLC analysis is performed on the isolated products, and compared to the standards for identification.

EXAMPLE 3

HPLC Analysis of Isolated Thiohydantoins

The isolated thiohydantoins were analyzed by HPLC, using a narrow-bore system (Model 120A, Applied Biosystems) using a PTH-C18 column (2.1 mm×22 cm, ABI) and a TFA-water-acetonitrile gradient system. The column was first equilibrated in A solvent (0.1% TFA in water, v/v), held in 100% A, 0% solvent B for 5 minutes after injection, then a linear gradient was developed to 40% B solvent (0.85% TFA in 70% acetonitrile) over 30 minutes. The percentage of B was then increased to 90% over 5 minutes, and held there for 20 minutes. The flow rate was 200 μl/min at ambient temperature. Effluent was monitored at 269 nm.

EXAMPLE 4

Synthesis of Thiohydantoin Standards

Standard samples for use in HPLC identification of residues were prepared as follows. One millimole of an FMOC-protected amino acid was weighed and placed into a stoppered flask with 1 millimole of diisopropylethylamine (DIPEA) and one equivalent of Woodward's Reagent K (both purchased from Aldrich Chemical Co.). The reaction mixture was allowed to stir at room temperature for 2-4 hours, until a homogenous solution formed. The solution was concentrated under vacuum, and the product FMOC-protected amino acid ester was dissolved in methylene chloride ($CH_2Cl_2$), dried over $MgSO_4$, and filtered. Next, a slight excess of trimethylsilylisothiocyanate (TMSITC) was added and the reaction mixture stirred overnight at room temperature. The FMOC-protected thiohydantoin was isolated by column chromatography (9:1 $CH_2Cl_2$:MeOH).

The FMOC protecting group was removed by stirring the purified thiohydantoin in a solution containing acetonitrile and 20% piperidine for 15 minutes at room temperature. Column chromatography of the product (same system) gave the purified thiohydantoin.

Although the invention has been described with reference to specific reactions, methods, and isothiocyanate reagents, it will be appreciated that a variety of changes and modifications can be made without departing from the invention.

It is claimed:

1. A method of forming an amino acid thiohydantoin comprising
    activating an N-protected amino acid with an N-substituted ketenimine to form the corresponding activated ester of the amino acid, and
    reacting the activated ester with a thiocarbonyl compound selected from the group consisting of a silylisothiocyanate and pyridinium thiocyanate to form the thiohydantoin of the amino acid.

2. The method of claim 1, wherein said activating includes generating the ketenimine by treating an N-alkyl isoxazolium compound with a base, and contacting the protected amino acid with ketenimine.

3. The method of claim 2, wherein said isoxazolium compound is N-alkyl-5'-alkyl or aryl isoxazolium.

4. The method of claim 3, wherein said isoxazolium compound is 2-ethyl-5'-phenylisoxazoliumsulfonate salt.

5. The method of claim 1, wherein said thiocarbonyl is a trialkylsilylisothiocyanate.

6. The method of claim 5, wherein said thiocarbonyl is trimethylsilylisothiocyanate.

7. The method of claim 1, wherein a N-alkyl isoxazolium compound is derivatized to a solid support, and said activating includes treating the support with a base, to generate a support with attached ketenimine group, and contacting the amino acid with the treated support.

8. The method of claim 7, wherein the N-alkyl isoxazolium compound is a 2-alkyl-5'-alkyl or aryl isoxazolium derivatized to the support through an N substituent.

9. The method of claim 1, wherein the amino acid contains a protected side chain, which further includes deprotecting the side chain in the activated ester of the amino acid, prior to reacting the ester with the thiocarbonyl compound.

10. The method of claim 1, for use in determining the C-terminal amino acid of an N-protected peptide, wherein the N-protected amino acid which is reacted with the ketenimine is the C-terminal residue of the peptide, said activating forms an activated ester at the C-terminal carboxyl group of the peptide, and said reacting includes contacting the activated ester with the thiocarbonyl to form a corresponding C-terminal peptidyl thiohydantoin, and cleaving the peptidyl thiohydantoin to release the C-terminal amino acid thiohydantoin from the residual peptide, and which further includes isolating and identifying the C-terminal amino acid thiohydantoin.

11. The method of claim 10, wherein said activating includes generating the ketenimine by treating an N-alkyl isoxazolium compound with a base, and contacting the protected amino acid with the ketenimine.

12. The method of claim 11, wherein said isoxazolium compound is derivatized to a solid support, and said activating includes treating the support with a base, to generate a support with attached ketenimine groups, and contacting the peptide with the support, thereby coupling the peptide to the support via an activated ester linkage, and said reacting releases the peptide from the support in the form of a C-terminal peptidyl thiohydantoin.

13. The method of claim 12, wherein said cleaving includes contacting the peptidyl thiohydantoin with a second solid support derivatized with a cleaving agent which is effective to cleave the peptidyl thiohydantoin to form the free C-terminal amino acid TH and the residual peptide.

14. The method of claim 13, wherein the second solid support is an ion exchange resin effective to selectively bind the residual peptide at selected ionic strength and pH conditions.

15. The method of claim 13, wherein the second solid support is derivatized with an oxime group effective to (a) cleave the peptidyl TH to form the free amino acid TH and (b) covalently bond to the residual peptide.

16. The method of claim 15, which further includes, following separation of the free amino acid TH from the second support, treating the second support to hydrolytically cleave the residual peptide from the support.

* * * * *